United States Patent [19]

Morgan

[11] Patent Number: 4,732,904
[45] Date of Patent: Mar. 22, 1988

[54] ANTIESTROGENIC HYDRAZONES

[76] Inventor: Lee R. Morgan, 725 Topaz St., New Orleans, La. 70124

[21] Appl. No.: 776,424

[22] Filed: Sep. 16, 1985

Related U.S. Application Data

[63] Continuation-in-part of Ser. No. 685,991, Dec. 24, 1984.

[51] Int. Cl.$^4$ .................. C07D 213/53; C07D 213/65; C07C 109/14; A61K 31/44
[52] U.S. Cl. ..................................... 514/357; 514/351; 514/639; 514/874; 546/300; 546/332; 260/349; 564/251
[58] Field of Search ............... 546/300, 332; 260/349; 564/251; 514/351, 357, 639

[56] References Cited

U.S. PATENT DOCUMENTS 4,418,068 11/1983 Jones .................................. 546/237

OTHER PUBLICATIONS

Dobek, A. S. et al, Antimicrobial Agents and Chemotherapy, Jul. 1980 (18, 1) pp. 27–36.
Chemical Abstracts 93:161813c (Dobeck et al).
Chemical Abstracts 94:120521h (Suginome et al).
Chemical Abstracts 93:247375y (McDonald et al).
Chemical Abstracts 95:17548u (Grases et al).
Chemical Abstracts 88:89215m (Nagai et al.).
Chemical Abstracts 94:8153p (Soria et al).
Shriner, R. L. et al, "Systematic Identification of Organic Compounds", 4th edition (1956), pp. 214–219, 316–319.
Chemical Abstracts 73:14634d (LeGoff et al.).
Chemical Abstracts 77:60926f (Brown et al).
Chemical Abstracts 89:110153x (Olsson et al).

*Primary Examiner*—Henry R. Jiles
*Assistant Examiner*—Dale A. Bjorkman
*Attorney, Agent, or Firm*—Klarquist, Sparkman, Campbell, Leigh & Whinston

[57] ABSTRACT

Azido-, 4-nitro and 2,4-dinitrophenylhydrazones as well as 4,4'-dihydroxybenzophenone-hydrazone and other hydrazones are disclosed which have antiestrogenic activity useful in treating estrogen-requiring tumor cells. The described hydrazones bind to estrogen receptors in the cytoplasm of tumor cells. The azido-, 4-nitro- and 2,4-dinitro-phenyl branches of the molecules appear to bind to the receptors and prevent translocation of estrogenic information into the nucleus, thereby blocking the synthesis of necessary macromolecules such as proteins. Absence of geometric isomerization from antiestrogenic to estrogenic forms of the drug minimizes estrogenic side-effects.

93 Claims, 10 Drawing Figures

ANTIESTROGENIC HYDRAZONES

CROSS REFERENCE TO RELATED APPLICATION

This is a continuation-in-part of Applicant's copending U.S. patent application Ser. No. 685,991, filed Dec. 24, 1984, the disclosure of which is incorporated by reference.

BACKGROUND OF THE INVENTION

1. Field of the Invention

This invention concerns antiestrogenic compounds useful for their antineoplastic properties.

2. Discussion of the Background of the Invention

Figure 1:
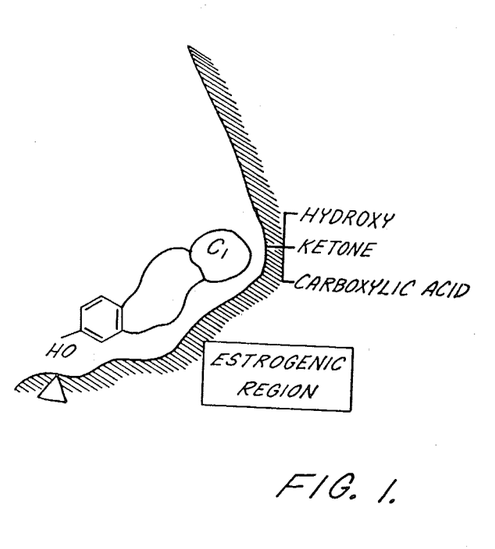
FIG. 1 is a schematic view of an estrogen binding to an estrogen receptor before the receptor undergoes an allosteric change that permits translocation of the estrogen-receptor complex to the nucleus.
Figure 2:
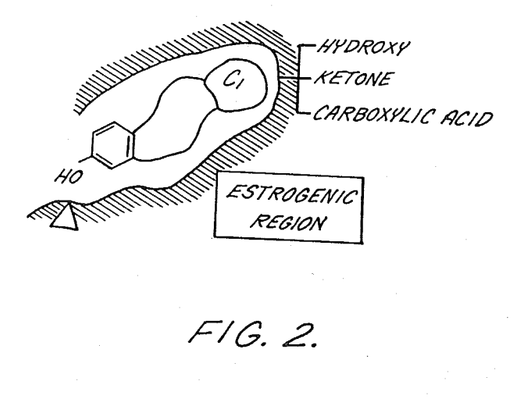
FIG. 2 is a view similar to FIG. 1 showing the receptor and estrogen after it has undergone an allosteric change and assumed the "cocoon-like" structure required for translocation of the complex to the nucleus.

Approximately 55% of all human breast cancers are considered to be estrogen dependent. This means that these tissues contain cells that bind estrogens through an absorption and transport mechanism that allows the entry of estrogens into the cell. It is believed that estrogen receptors (which are proteins) originate in the cytoplasm of cells and initially interact with extracellular estrogens in the cell membranes to bind the estrogen to the protein receptor, as shown in FIG. 1. The protein receptor then folds on the estrogen to form a "cocoon-like" structure, thereby completing the tertiary structure of the receptor complex which stimulates the translocation of the receptor-estrogen complex through the pores of the nuclear membrane. The receptor protein must undergo an allosteric change in its conformation before the complex has the ability to bind to DNA. A hypothetical structure for such a tertiary estrogen-protein receptor complex which has undergone an allosteric change and assumed the "cocoon-like" structure is shown in FIG. 2.

The receptor protein must undergo this allosteric change in its conformation before the complex has the ability to bind to DNA. Once inside the nucleus, the activated receptor initiates transcription of genetic information from the DNA thereby forming m-RNA which is in turn a template for the linking of amino acids into proteins needed for cell membrane replication.

The antiestrogen effects produced by drugs such as tamoxifen (Nolvadex ®) appear to be one of preventing the estrogen receptor from interacting with DNA in the nucleus to stimulate RNA and protein synthesis. This action initiates a block in the synthesis of macromolecules such as proteins, causing cell damage and ultimate death of the cell.

Antiestrogens are believed to be lipophilic molecules having a portion of the molecule which resembles naturally occurring estrogens. This portion of the antiestrogen selectively binds to the estrogen receptors. The antiestrogens, however, have a side chain arm (e.g. dimethylaminophenyl ethoxy) which distorts the three-dimensional configuration of the estrogen receptor preventing translocation of the receptor to the nucleus (see FIG. 3). A tertiary complex between chemical and receptor cannot form, thus cytoplasmic proteins which are usually synthesized in response to the translocation of the estrogen receptor are accordingly not produced, the cells are not able to replicate, and they die. Therefore, any agent that interferes with the final complex of drug and receptor ties up the receptor and prevents estrogen from entering the cells and/or blocks the DNA-RNA-protein cascade.

Figure 3:
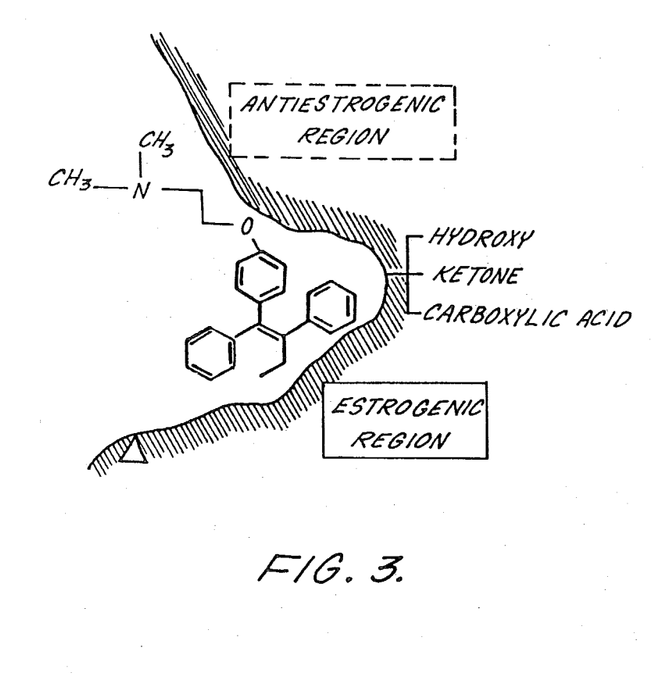
FIG. 3 is a schematic view of the tamoxifen molecule bound to the protein receptor, the dimethyl-amino side chain preventing the receptor molecule from undergoing the allosteric change required for translocation to the nucleus.
Figure 4:
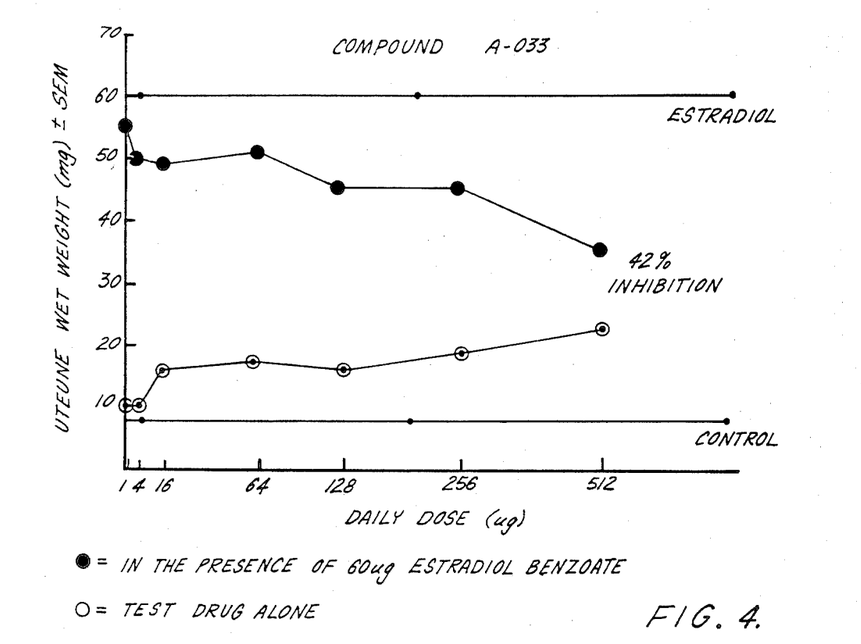
FIG. 4 is a graph showing the uterotrophic activity and anti-uterotrophic activity of test compound A-033, (biphenyl methylene-2,4-dinitrophenylhydrazone). For all graphs the upper line is for estradiol stimulation alone and represents the mean uterine net weight (60 mg) of the uterus of a rat which has received an injection of 0.64 ug of estradiol benzoate; the line below that represents the antiestrogenic effect of the compound; the next lower line represents the compound's estrogenic effects while the bottom line represents the control weight of an unstimulated uterus.
Figure 5:
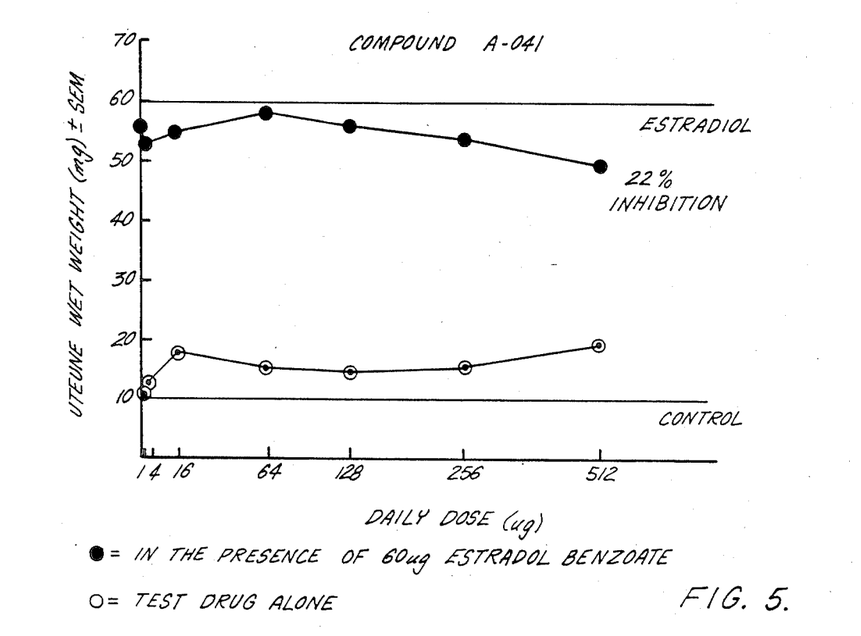
FIG. 5 is a graph similar to FIG. 4 showing the uterotrophic and anti-uterotrophic activitiy of compound A-041, (4,4'-dimethoxy biphenyl methylene-2,4-dinitrophenylhydrazone).
Figure 6:
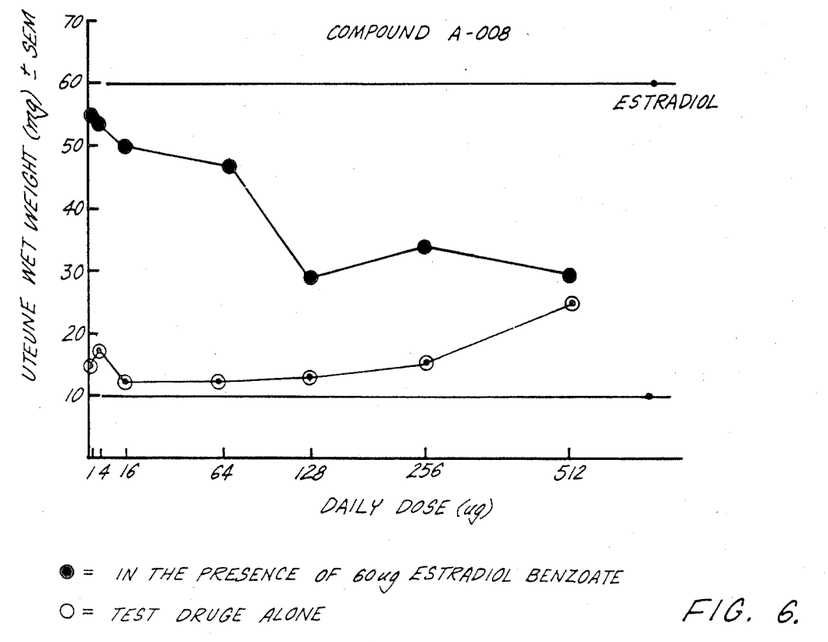
FIG. 6 is a graph similar to FIG. 4 showing the uterotrophic and anti-uterotrophic activity of compound A-008, (4-hydroxyacetophenone-2,4-dinitrophenylhydrazone).
Figure 7:
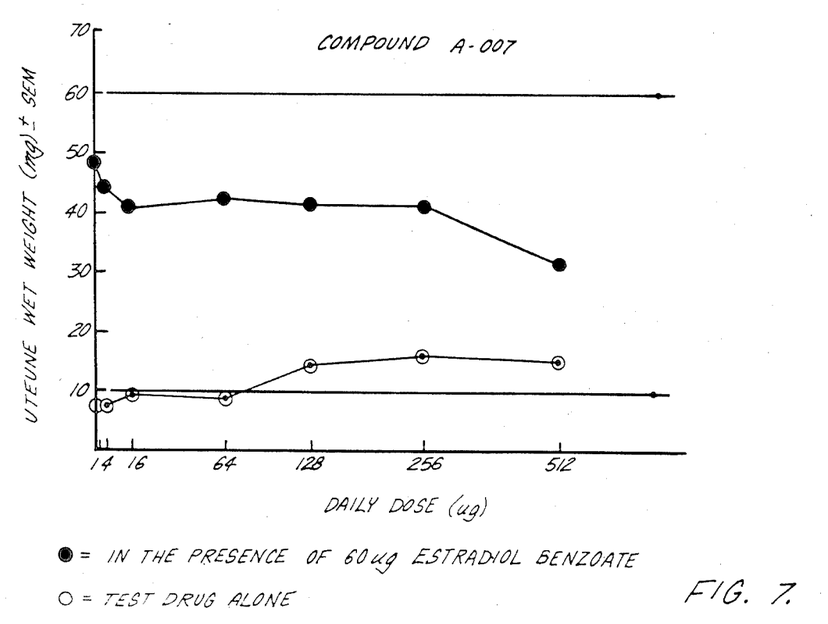
FIG. 7 is a graph showing the uterotrophic and anti-uterotrophic activity of compound A-007, (4,4'-dihydroxybiphenylmethylene-2,4-dinitrophenylhydrazone).
Figure 8:
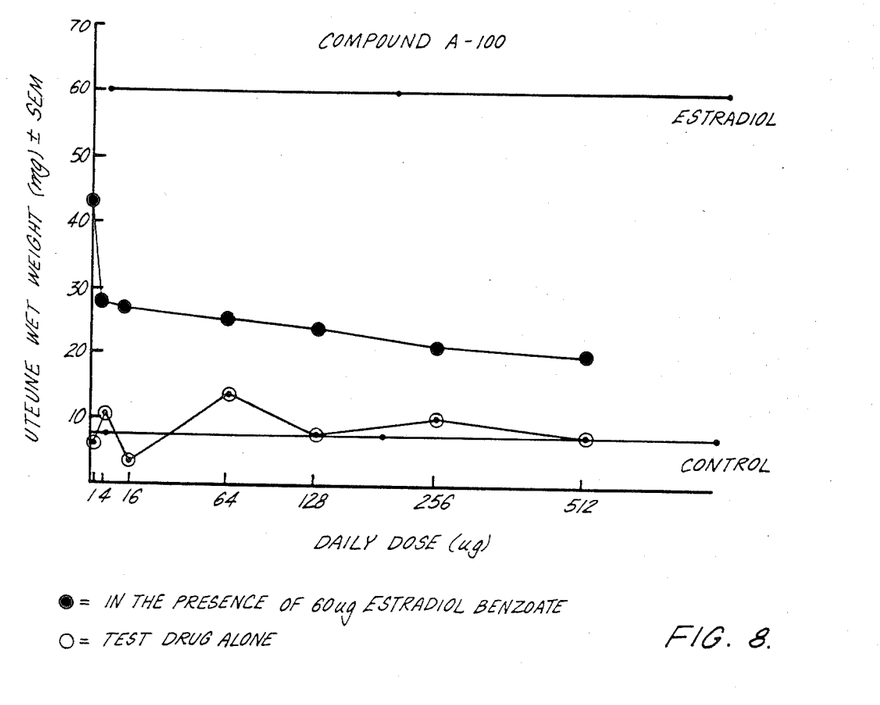
FIG. 8 is a graph showing the uterotrophic and anti-uterotrophic activity of compound A-100 (4,4'-dihydroxybiphenylmethylene-4-nitrophenylhydrazone).
Figure 9:
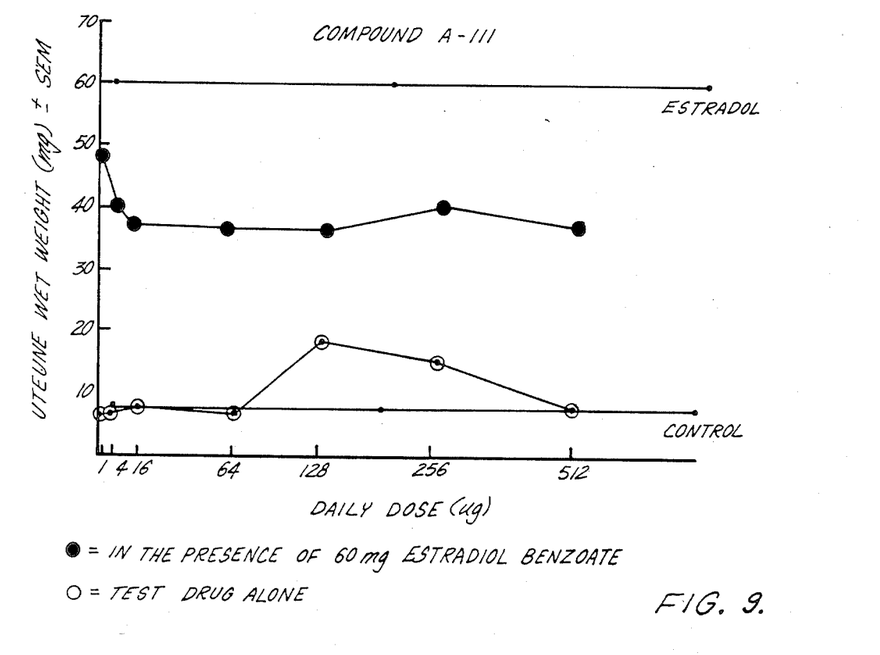
FIG. 9 is a graph showing the uterotrophic and anti-uterotrophic activity of compound A-111, (4,4'-dihydroxybiphenylmethylene-4-azido-phenylhydrazone).

FIG. 3 shows an estrogen receptor occupied by tamoxifen wherein the dimethyl amino side chain arm prevents the receptor from forming the "cocoon-like" structure that was shown in FIG. 2. Prevention of this allosteric tertiary change prevents translocation of the occupied receptor to the nucleus.

Antiestrogens are useful in impairing growth and/or destroying estrogen dependent tumor cells because such cells require estrogen hormones for growth.

Tamoxifen (Nolvadex ®) is a non-steroidal estrogen antagonist which is currently used in the treatment of breast cancer. The tamoxifen molecule binds to the receptor, but tamoxifen contains a dimethyl-aminophenyl ethoxy arm which apparently distorts the three-dimensional shape of the receptor molecule and inhibits the translocation of estrogenic information to the nucleus. Unfortunately, tamoxifen undergoes an isomerization under physiological conditions from the therapeutically useful trans configuration (antiestrogenic) to a cis form of the drug (estrogenic). This is a serious drawback since the antiestrogenic compound, after isomerization to an estrogenic compound, begins satisfying the estrogenic requirements of the tumor cell. In addition, the presence of an estrogen-like substance in the body results in stimulation of hypertrophy of the uterine endometrium with intermittent vaginal bleeding, especially in elderly females in whom the agent is most effective. In addition, tamoxifen is not an effective anti-cancer agent in the presence of physiological amounts of estradiol in an estrogen dependent human breast cancer cell line (ZR-75-1).

Most of the other available antiestrogens also have geometric centers about which trans/cis isomerization occurs. They accordingly undergo isomerization and have both estrogenic and anti-estrogenic properties. Other experimental antiestrogenic agents have the additional drawback of containing an ethyl pyrrolidine group (Lilly's Ly 156758 and Upjohns' Nafoxadine) which causes allergic reactions, such as corneal ulceration, in sensitive human individuals.

It is an object of the present invention to provide antiestrogenic compounds which do not undergo isomerization to an estrogenic compound under physiological conditions.

It is another object of the present invention to provide compounds with minimum estrogenic activity which thereby reduces endometrial stimulation and hypertrophy of the uterus.

It is also an object of the invention to provide an antiestrogen having minimal allergic side effects.

SUMMARY OF THE INVENTION

The aforementioned objects are achieved by providing hydrazones of the following structure:

TABLE 1

| NO. WHERE: | R | R$^1$ | R$^2$ | X |
|---|---|---|---|---|
| A-008 | HO | C | CH$_3$ | C$_6$H$_3$—2,4(NO$_2$)$_2$ |
| A-113 | HO | C | C$_6$H$_4$OH | H |
| A-033 | H | C | C$_6$H$_5$ | C$_6$H$_3$—2,4(NO$_2$)$_2$ |
| A-077 | HO | C | C$_6$H$_4$OH | C$_6$H$_3$—2,4(NO$_2$)$_2$ |

TABLE 1-continued

| NO. WHERE: | R | R¹ | R² | X |
|---|---|---|---|---|
| A-041 | CH₃O | C | C₆H₄OCH₃ | C₆H₃—2,4(NO₂)₂ |
| A-061 | H | N | C₆H₃—3,4-(OCH₃)₂ | C₆H₃—2,4(NO₂)₂ |
| A-100 | HO | C | C₆H₄OH | C₆H₄—4(NO₂) |
| A-111 | HO | C | C₆H₄OH | C₆H₄—4(N₃) |

These compounds have a ring structure portion which steriochemically can occupy the estrogenic region of estrogen receptors, while the substituted phenyl arm steriochemically inhibits the receptor from undergoing an allosteric change to prevent translocation of estrogenic information to the nucleus. The electron rich density of the azido-, mono- and di-nitrophenyl and simple hydrazones provides sufficient electron density for long-lasting binding that permits less frequent administration of the drug while still achieving therapeutic objectives.

The novel compounds of the invention can be summarized as follows:

In preferred embodiments, a therapeutically effective amount of the compound is suspended in a pharmaceutically inert carrier such as peanut oil. In other embodiments, the compound can be made into a pill for oral administration. The compound could also be combined with an aqueous vehicle for injection. In other important embodiments the compound can be placed in solvents such as propylene glycol, dimethylsulfoxide (DMSO) or mixtures thereof and applied topically to tumor recurrences, such as occur with breast tumors after surgery.

The group of compounds described, in addition to their anti-estrogenic tumor activity, will inhibit estrogen interaction in the pituitary and thus stimulate the release of follicle stimulating hormone (FSH) and luteinizing hormone (LH) resulting in ovulation. This is of importance in infertility problems, and the compound can accordingly be used to induce ovulation and permit conception to occur. The same dosages employed in connection with anti-tumor activity of the compound will be sufficient for use of the compound to induce ovulation.

In especially preferred embodiments of the compound, R is hydroxy, R¹ is hydroxyphenyl, and X is hydrogen.

In other preferred embodiments, R is hydrogen, hydroxy or methoxy; R¹ is carbon or nitrogen; R² is methyl, phenyl, hydroxyphenyl, or methoxyphenyl; and X is hydrogen.

Another preferred embodiment of the compound is formed when R is hydroxy, R¹ is carbon or nitrogen, R² is methyl, phenyl, hydroxyphenyl, methoxyphenyl, or dimethoxyphenyl and X is hydrogen, azidophenyl, aminophenyl, nitro or dinitrophenyl.

Another preferred embodiment is formed when R is hydrogen, hydroxy or methoxy; R¹ is nitrogen; R² is methyl, phenyl, hydroxyphenyl, or methoxyphenyl; X is hydrogen, azidophenyl, aminophenyl, nitro or dinitrophenyl.

Still another preferred embodiment is formed when R is hydrogen, hydroxy or methoxy; R¹ is carbon or nitrogen; R² is methyl, phenyl, hydroxyphenyl, or methoxyphenyl, and X is azidophenyl.

Yet another preferred embodiment is formed when R is hydrogen, hydroxy or methoxy; R¹ is carbon or nitrogen; R² is methyl, phenyl, hydroxyphenyl or methoxyphenyl; and X is aminophenyl.

A better understanding of these preferred embodiments can be had by reference to the following drawings and detailed description of how to make and use the instant invention.

DETAILED DESCRIPTION

Molecular Structure

The following compounds have been synthesized, and their molecular structures are shown as follows:

4-Hydroxyacetophenone-2,4-dinitrophenylhydrazone (A-008)

Empirical formula $C_{14}H_{12}N_4O_5$
Molecular weight: 316
Melting point: 240°–241° C.
solubility: Ethanol, methanol, acetone
Physical description:
Red crystals
Recrystallized from methanol/acetone
Anal. calc: C, 53.22; H, 3.87; N, 17.71, Found: C, 53.28; H, 3.82; N, 17.55.

Biphenyl methylene-2,4 dinitrophenylhydrazone (A-033)

Empirical formula: $C_{19}H_{14}O_4N_4$
Molecular weight: 363
Melting point: 245° C.
Solubility: Conc. acetic acid, ethanol
Physical Description: Red Crystals
Anal. calc: C, 62.98; H, 3.86; N, 15.46, Found: C, 63.17; H, 4.06; N, 15.49.

4,4'-Dihydroxybiphenyl-methylene-2,4-dinitrophenylhydrazone. (A-007)

Empirical formula: $C_{19}H_{14}N_4O_6$
Molecular weight: 394
Melting point: 240°–241° C.
Soluble: Ethanol, methanol, acetone; insoluble in water
Physical description:
Red crystals
Recrystallized from ethanol
Anal. calc: C, 57.86; H, 3.55; N, 14.21, Found: C, 56.42; H, 3.81; N, 13.88.

4,4'-Dimethoxy Diphenylmethylene-2,4-dinitrophenylhydrazone(A041)

Empirical formula: $C_{21}H_{18}N_4O_6$
Molecular weight: 422
Melting Point: 205° C.
Solvent: Ethanol, methanol
Description: Red Needles
Anal. calc: C, 59.71; H, 4.26; N, 13.27, Found: C, 59,85; H, 4.33; N, 13.36.

3,4-Dimethoxybenzyl-(2-piperidyl)-2,4-dinitrophenylhydrazone (A-061):

Empirical formula: $C_{20}H_{17}O_6N_5$
Molecular weight: 423
Melting point: 230°–232° C.
Solubility: Methanol, water
Physical description: Fine orange powder
Anal. calc: C, 56.7; H, 4.0; N, 16.5, Found: C, 56.5; H, 3.9; N, 16.7.

4-Methoxybenzyl-(2-piperidyl)-2,4-dinitrophenylhydrazone (A-077):

Empirical formula: $C_{19}H_{15}N_5O_5$
Molecular weight: 393
Melting point: 230° C.
Solubility: Methanol, water
Physical description: Fine red powder
Anal. calc: C, 58.02; H, 3.82; N, 17.81, Found: C, 58.15; H, 3.77; N, 17.89.
4,4′-Dihydroxybiphenyl-methylene-4-nitrophenylhydrazone (A-100).

Empirical formula $C_{19}H_{15}N_3O_4$
Molecular weight: 349
Melting point: 245°–248° C. with dec.
Solubility: Ethanol, methanol, acetone; insoluble in water
Physical description: Red-Orange crystals Recrystallized from ethanol
Anal. calc: C, 65.33; H, 4.29; N, 12.03, Found: C, 65.13; H, 4.19; N, 12.14.
4,4′-Dihydroxybiphenyl-methylene-4-azidohydrazone (A-111).

Empirical formula: $C_{19}H_{15}N_5O_2$
Molecular weight: 345
Melting point: 196°–197°
Solvent: Ethanol, methanol
Physical Description: Yellow amorphous powder
Anal. calc: C, 66.08; H, 4.35; N, 20.28, Found: C, 66.12; H, 4.42; N, 13.51.
4,4′-Dihydroxybenzophenone Hydrazone (A-113)

Empirical formula: $C_{13}H_{12}N_2O_2$
Molecular weight: 228
Melting point: 210°–215°
Solvent: Ethanol, methanol
Physical Description: Yellow crystals
Anal. calc: C, 66.42; H, 5.26; N, 12.28, Found: C, 68.37; H, 5.42; N, 12.24.

SYNTHESIS

Several groups of hydrazones have been synthesized and tested. Their synthesis is summarized in the table below.

The following ketone starting materials in Table 2 were obtained from Aldrich or Sigma Chemical Company: for A-008, 4-hydroxyacetophenone; for A-033, benzophenone; for A-007 & A-100, 4,4′-dihydroxybenzophenone; for A-041, 4,4′dimethoxybenzophenone. Some phenylhydrazones which required synthesis or starting materials were for A-061, 3,4-dimethoxybenzyl (2-pyridyl) ketone; for A-077, 4-methoxybenzyl (2-pyridyl) ketone; and for A-111, 4,4′dihydroxybiphenyl-methylene-4-azidohydrazone. The last three compounds were synthesized as below.

4-Methoxybenzyl(2-pyridyl) carbinol (for A-077)

Ketone starting material for A-077 was prepared from picolinic acid and 4-methoxybenzaldehyde. To a solution of 50 g. (0.37 moles) of 4-methoxybenzaldehyde and 50 ml. p-cymene (heated to dissolve) in a 3-neck flask with reflux condenser and refluxed until boiling, 10 g. (0.08 moles) picolinic acid was added dropwise and then refluxed for three hours. The solution changed in color from reddish to brown at the end. The solution was cooled and extracted in a separatory funnel with 2 N HCl (twice with 50 ml.). The above acid layer was washed twice with 100 ml. diethyl ether. The ether layer was discarded. The acid layer was basified with ice cold concentrated ammonium hydroxide at 0° C. The basic layer was extracted with diethyl ether (3×100 ml.) until clear. The ether washings were collected and dried over anhydrous sodium sulfate. The filtered ethereal solutions were evaporated (under rotovacuum) at room temperature until an oil formed. The oil was dissolved in minimal ethanol to solubilize, and hot water dropwise was added until turbidity was produced and then disappeared on further heating. On cooling, a cloudy layer formed an oil which was removed by hand aspiration rapidly because it precipitated quickly. The 4-methoxybenzyl(2-pyridyl) carbinol oil was recrystallized from ethanol-water (80:20) as a white powder, 65% yield, mp 110°–112° C. Calc. for $C_{14}H_{13}NO_2$: C, 74.01; H, 5.73; N, 6.16. Found: C, 74.09; H, 6.01; N, 6.04.

4-Methoxybenzyl(2-pyridyl) ketone (for A-077)

The carbinol, 10 g. (0.04 moles), synthesized in the above scheme, was dissolved in 200 ml. of water. To the solution, 5 g. of potassium permanganate in 200 ml. of water was slowly added with stirring maintaining the solution at 20° C. The solution was stirred for another 30 minutes. After the solution changed color, 30 ml. of ethanol were slowly added dropwise directly to the oxidized solution and stirred for an additional 10 minutes. The mixture was filtered until clear and evaporated to 75% of original volume under vacuum, and let stand in the cold. On standing, a white powder formed which recrystallized from methanol, mp 93°–94° C. Yield 36%. Anal. Calc. for $C_{14}H_{11}N_1O_2$: Calc. C, 69.13; H, 5.34; N, 5.76. Found, C, 68.92; H, 5.53; N, 5.60.

3,4-Dimethoxybenzyl (2-pyridyl) carbinol (for A-061)

Starting material for A-061 was prepared from picolinic acid and 3,4-dimethoxybenzaldehyde. To a solution of 50 g. (0.3 moles) of 3,4-dimethoxybenzaldehyde and 50 ml. p-cymene (heated to dissolve), 10 g. (0.08 moles) of picolinic acid was added dropwise at boiling reflux and then further refluxed for 3 hours. The solution became a reddish-brown at the end. The solution was cooled and extracted twice with 50 ml. of 2N HCL. The extracted layer was washed twice with 100 ml. of diethyl ether and the ether layer discarded. The acid layer was neutralized with ice cold concentrated ammonium hydroxide at 0° C. The neutralized layer was then extracted with diethyl ether (100 ml.×2) and the etheral layer saved and dried over anyhydrous sulfate. The ether layer was evaporated until an oil formed. The oil was dissolved in minimal ethanol-water, cooled, and in 1–4 days at 5° C., cream colored crystals formed; mp 93°–94° C. Yield: of 3,4-dimethoxybenzyl(2-pyridyl) carbinol was 30%. Anal. calc. for $C_{14}H_{15}O_3N_1$: Calc. C, 68.6; H, 6.11; N, 5.70. Found: C, 68.77, 6.29, and N, 5.68.

3,4 Dimethoxybenzyl(2-pyridyl) ketone

To 10 g. (0.04 moles) of the carbinol synthesized in the previous step, was added slowly with stirring, 5 g. of potassium permanganate in 200 ml. water at 20° C. The solution was stirred for another 30 minutes. After the color changed, 30 ml. of ethanol were added directly to the oxidized solution and stirred for an additional 10 minutes. The mixture was filtered until clear and evaporated to 75% of the original volume under vacuum and allowed to stand in the cold. On standing, a fine white powder formed which was recrystallized from aqueous ethanol, Yield: 65%; mp 93°–94° C. Calc. anal. for $C_{14}H_{14}O_3N_1$: Calc. C, 69.13; H, 5.34; N, 5.76. Found: C, 68.92; H, 5.53; and N, 5.60.

4,4'-dihydroxybiphenyl-methylene-4-azidophenylhydrazone for (A-111)

Sodium hydrosulfite (8 g.) was added slowly under vigorous stirring to a refluxing solution of 1.12 g (0.0032 mole) of A-100 in 300 ml. of acetone, 60 ml. of water and 60 ml. of 1N sodium hydroxide. Refluxing was continued after the addition of sodium hydrosulfite was completed. The solution changed color from deep purple to deep orange in 30–40 minutes of stirring with reflux. To the solution 100 ml. of water was added. While still warm most of the acetone was removed under vacuum. The solution was neutralized with 10% acetic acid. After refrigeration overnight the reddish-orange precipitate was filtered, washed with cold water and dried. The crystals were recrystallized from 50% ethanol as orange needles (m.p. 172°–179°) of 4,4'-dihydroxy biphenyl-methylene-4-amino phenylhydrazone. Yield was 400 mg. (37%). Anal for $C_{19}H_{17}N_3O_2$: Anal. calc: C, 68.89.; H, 5.14; N, 12.69. Found: C, 68.92; H, 5.61; N, 12.42.

The above amine (1.8 g., 0.0054 mole) was suspended in 8 ml. of 12N hydrochloric acid and cooled in a methanol-ice bath to −10° C. To this solution 0.6 g. of sodium nitrite (0.0087 mole) in 3 ml. of water was added slowly with stirring and not allowing the temperature to rise above 0° C. Then 8 ml. of cold (0° C.) glacial acetic acid was added after which 0.6 g. of sodium azide (0.0092 mole) in 2.5 ml. of water was added dropwise, with stirring, at a rate slow enough to keep the temperature below 10° C. All reactions subsequent to azide formation were carried out in vessels shielded from light. After the sodium azide was added, 15 ml. of cold water was added and the reaction mixture was stirred an additional 30 minutes. The product was a yellow-tan precipitate. The reaction mixture was then diluted to 100 ml. with cold water and the product removed by filtration. The product was washed with cold water and then air dried. The yield was 800 mg. (43%). The m.p. was 196°–197°.

Anal for $C_{19}H_{15}N_5O_2$: Calc. C, 66.08; H, 4.35; N, 20.28. Found: C, 66.12; H, 4.42; N, 13.51.

The following general procedures were employed for the synthesis of the phenylhydrazones:

TABLE 2

| COMPOUNDS | STARTING MATERIALS | |
|---|---|---|
| A-008 | 4-hydroxyacetophenone | 2,4-dinitrophenylhydrazine |
| A-033 | benzophenone | 2,4-dinitrophenylhydrazine |
| A-007 | 4,4'-dihydroxybenzophenone | 2,4-dinitropheylhydrazine |
| A-100 | 4,4'-dihydroxybenzophenone | 4-nitrophenylhydrazine |
| A-041 | 4,4'-dimethoxybenzophenone | 2,4-dinitrophenylhydrazine |
| A-061 | 3,4-dimethoxybenzyl-(2-pyridyl)-ketone | 2,4-dinitrophenylhydrazine |
| A-077 | 4-methoxybenzyl (2-pyridyl)-ketone | 2,4-dinitrophenylhydrazine |
| A-111 | 4,4'-dihydroxybiphenyl-methylene-4-azidohydrazone | |
| A-113 | 4,4'-dihydroxybenzophenone | hydrazine |

Procedure 1:

4-Nitro- or 2,4-dinitrophenylhydrazine (0.0016 moles) was suspended in 5 ml. of methanol. The 4-nitrophenylhydrazine was used if the 4-nitrophenylhydrazone product was being prepared while the 2,4-dinitrophenylhydrazine was used if a 2,4-dinitrophenylhydrazone was being prepared. Dropwise, 0.4–0.5 ml. of concentrated sulfuric acid was cautiously added with stirring and the warm solution filtered. A solution of the carbonyl compound (0.0016 moles) in 5–20 ml. of methanol or ethanol was added dropwise to twice the above phenylhydrazine solution. If no solid separated from the reddish colored solution within 10 minutes, the solution was carefully diluted with 5–20 ml. of 2N sulfuric acid. The solid was collected by suction filtration and washed with a little cold methanol. The derivative was recrystallized from ethanol, methanol or dilute acetic acid according to Table 2.

Procedure 2:

4-Nitro- or 2,4-dinitrophenylhydrazine 2.5 g (0.016 moles) was dissolved in 30 ml. of 85 percent phosphoric acid. The solution was diluted with 20 ml. of 95 percent ethanol, allowed to stand and then filtered.

The carbonyl compound (0.008 moles) was dissolved in 10–40 ml. of ethanol and the calculated volume of the above reagent added, to produce a 2:1 rate of the 4-nitro- or 2,4-dinitrophenylhydrazine and ketone, respectively. If a precipitate did not form immediately, it ws diluted with a little water. The derivative was collected and recrystallized according to Table 2.

Hydrazone of 4,4'-Dihydroxybenzophenone (A-113)

The method of synthesizing the hydrazone of 4,4'-dihydroxybenzophenone (A-113) required a slightly different synthesis as follows: a mixture of 10.4 g (0.08 mole) of hydrazine sulfate, 22 g (0.16 mole) of sodium acetate and 50 g of water is boiled five minutes, cooled to about 50° and 55 ml of methyl alcohol added. The precipitated sodium sulfate is filtered and washed with a little methanol.

A hot solution of 5.1 g (0.024 mole) of 4,4'-dihydroxybenzophenone in 15 ml of methanol was added dropwise with stirring to the above solution of hydrazine at 60° C.

After the addition of the dihydroxybenzophenone, the yellow solution was refluxed with stirring for one hour. On cooling additional sodium sulfate precipitated and was filtered. Water was added slowly until turbid. On standing in a refrigerator over two days yellow crystals formed. Yield 72%, m.p. 210°–215°. Recrystallized from ethanol.

Anal. calc. for $C_{13}H_{12}N_2O_2$: C, 68.42; H, 5.26; N, 12.28. Found: C, 68.37; H, 5.42; N, 12.24.

ESTROGENIC-ANTIESTROGENIC ACTIVITIES

The discovery of estrogenic receptors in human breast cancer cells has provided a useful tool in determining the therapeutic utility of specific endocrine agents. The endocrine receptor assay is an extremely powerful tool for predicting the response to endocrine treatments since endrocrine receptors specifically concentrate estrogens into the target tissues. DeSombre et al., Steroid Receptors in Breast Cancer, New England J. of Med., 301: 1011–1012, 1979; J. H. Clark et al., Female Sex Steroids Receptors and Function, Monographs on Endocrinology, Vol. XIV, Berlin, Springer Verlag, 1979.

Estrogenic activity of the claimed compounds in the uterus was determined by employing the wet uterine weight of the immature (3-week-old) Sprague Dawley rat. Rats were sacrificed after three consecutive days of i.p. administration of test compounds at the specified doses. The mean control (unstimulated) uterine weight for a 21-day-old rat is 10 mg. Five to ten animals were employed at each dose level. The purpose of this test was to determine the estrogenic activity of each of the test compounds. Estrogenic activity can be determined by comparing the net uterine weight of the test animals to which the compounds were administered with the 10 mg. mean weight of rats not being injected with the drug. All drugs and estrogens were dissolved in peanut oil.

Antiestrogen activity in rat uterii was determined by giving 0.64 ug. of estradiol benzoate plus the test drug to immature Sprague Dawley rats at specified doses concomitantly i.p. for three days. Rats were sacrificed and uterii weighed. Estradiol benzoate alone produces a mean weight of 60 mg. in this system. Five to ten animals were employed at each dose level.

The data and graphs concerning uterotrophic activity demonstrate the relative activities of the test compounds in stimulating uterine growth. Such stimulation of uterine growth is a measurement of the test compounds' estrogenic activity. Such activity is undesirable since it causes side effects and may satisfy the estrogenic requirements of estrogen dependent tumor cells.

The data and graphs concerning antiuterotrophic activity demonstrate the ability of the test compounds to inhibit stimulation of uterii which have been already stimulated by administration of 0.64 ug of estradiol benzoate to the test animal. A Sprague Dawley Rat receiving this dose of estradiol benzoate has a mean wet weight uterus of 60 mg. Percent inhibition of stimulation is measured by comparing the stimulated uterine weight (60 mg) with the uterine weight wherein estradiol benzoate and the test compound are administered concomitantly.

The data regarding estrogenic (or uterotrophic) activities and antiestrogenic (antiuterotrophic activities) for compounds A-008, 007, 033, 041, 061, 100, 111 and 113 in comparison to tamoxifen are shown in the following tables and FIGS. 4–9.

ANIMAL STUDIES
TAMOXIFEN - CONTROL
UTEROTROPHIC ACTIVITIES IN IMMATURE FEMALE
(3-wk.old) SPRAGUE DAWLEY RATS

| | UTEROTROPHIC ACTIVITY | |
|---|---|---|
| Drug Dose (ug) | $\overline{M}$ wet wt. uterus (mg) | Ratio Drug/Estradiol |
| 1 | 23. | .34 |
| 4 | 25.1 | .42 |
| 16 | 29.2 | .58 |
| 64 | — | .52 |
| 128 | 17.1 | .43 |
| 256 | 25.5 | .48 |
| 512 | 21.2 | — |

| | ANTI-UTEROTROPHIC ACTIVITY (In the Presence of 60 ug of Estradiol Benzoate) | |
|---|---|---|
| Drug Dose (ug) | $\overline{M}$ wet wt. uterus (mg) | Percent Inhibition |
| 1 | 40.3 | 0 |
| 4 | 35.3 | 19 |
| 16 | 30.5 | 37 |
| 64 | 30.3 | 38 |
| 122 | 27.6 | 48 |
| 256 | 21.6 | 71 |
| 512 | — | — |

$\overline{M}$ Control - 14 mg
$\overline{M}$ Estradiol - 40 mg

A-008
UTEROTROPHIC ACTIVITIES IN IMMATURE FEMALE
(3-wk.old) SPRAGUE DAWLEY RATS

| | UTEROTROPHIC ACTIVITY | |
|---|---|---|
| Drug Dose (ug) | $\overline{M}$ wet wt. uterus (mg) | Ratio Drug/Estradiol |
| 1 | 14 | 0.23 |
| 4 | 17 | 0.28 |
| 16 | 12 | 0.20 |
| 64 | 12 | 0.20 |
| 128 | 13 | 0.22 |
| 256 | 16 | 0.27 |
| 512 | 25 | 0.42 |

| | ANTI-UTEROTROPHIC ACTIVITY (In the presence of 60 ug of Estradiol Benzoate) | |
|---|---|---|
| Drug Dose (ug) | $\overline{M}$ wet wt. uterus (mg) | Percent Inhibition |
| 1 | 54 | 12 |
| 4 | 53 | 14 |
| 16 | 50 | 20 |
| 64 | 47 | 26 |
| 128 | 28 | 64 |
| 256 | 34 | 52 |

A-008
UTEROTROPHIC ACTIVITIES IN IMMATURE FEMALE
(3-wk.old) SPRAGUE DAWLEY RATS

| 512 | 30 | 60 |
|---|---|---|

$\overline{M}$ Control - 10 mg
$\overline{M}$ Estradiol - 60 mg

A-033
UTEROTROPHIC ACTIVITIES IN IMMATURE FEMALE
(3-wk.old) SPRAGUE DAWLEY RATS

| | UTEROTROPHIC ACTIVITY | |
|---|---|---|
| Drug Dose (ug) | $\overline{M}$ wet wt. uterus (mg) | Ratio Drug/Estradiol |
| 1 | 8 | 0.13 |
| 4 | 10 | 0.17 |
| 16 | 16 | 0.27 |
| 64 | 17 | 0.28 |
| 128 | 16 | 0.27 |
| 256 | 17 | 0.28 |
| 512 | 23 | 0.38 |

| | ANTI-UTEROTROPHIC ACTIVITY (In the Presence of 60 ug of Estradiol Benzoate) | |
|---|---|---|
| Drug Dose (ug) | $\overline{M}$ wet wt. uterus (mg) | Percent Inhibition |
| 1 | 56 | 8 |
| 4 | 50 | 20 |
| 16 | 48 | 24 |
| 64 | 50 | 20 |
| 128 | 45 | 30 |
| 256 | 44 | 50 |
| 512 | 35 | 50 |

$\overline{M}$ Control - 10 mg
$\overline{M}$ Estradiol - 60 mg

A-007
UTEROTROPHIC ACTIVITIES IN IMMATURE FEMALE
(3-wk.old) SPRAGUE DAWLEY RATS

| | UTEROTROPHIC ACTIVITY | |
|---|---|---|
| Drug Dose (ug) | $\overline{M}$ wet wt. uterus (mg) | Ratio Drug/Estradiol |
| 1 | 7 | 0.12 |
| 4 | 7 | 0.12 |
| 16 | 9 | 0.15 |
| 64 | 8 | 0.13 |
| 128 | 14 | 0.23 |
| 256 | 16 | 0.27 |
| 512 | 15 | 0.25 |

| | ANTI-UTEROTROPHIC ACTIVITY (In the presence of 60 ug of Estradiol Benzoate) | |
|---|---|---|
| Drug Dose (ug) | $\overline{M}$ wet wt. uterus (mg) | Percent Inhibition |
| 1 | 48 | 24 |
| 4 | 44 | 32 |
| 16 | 41 | 38 |
| 64 | 43 | 34 |
| 128 | 42 | 36 |
| 256 | 42 | 36 |
| 512 | 32 | 56 |

$\overline{M}$ Control - 10 mg
$\overline{M}$ Estradiol - 60 mg

A-113
UTEROTROPHIC ACTIVITIES IN IMMATURE FEMALE
(3-wk.old) SPRAGUE DAWLEY RATS

| | UTEROTROPHIC ACTIVITY | |
|---|---|---|
| Drug Dose (ug) | $\overline{M}$ wet wt. uterus (mg) | Ratio Drug/Estradiol |
| 1 | 7 | 0.12 |
| 4 | 7 | 0.12 |
| 16 | 9 | 0.15 |
| 64 | 8 | 0.13 |
| 128 | 10 | 0.17 |
| 256 | 14 | 0.23 |
| 512 | 15 | 0.25 |

| | ANTI-UTEROTROPHIC ACTIVITY (In the presence of 60 ug of Estradiol Benzoate) | |
|---|---|---|
| Drug Dose (ug) | $\overline{M}$ wet wt. uterus (mg) | Percent Inhibition |
| 1 | 48 | 24 |
| 4 | 44 | 32 |
| 16 | 41 | 38 |
| 64 | 43 | 34 |
| 128 | 38 | 44 |
| 256 | 39 | 42 |
| 512 | 32 | 56 |

$\overline{M}$ Control - 10 mg
$\overline{M}$ Estradiol - 60 mg

A-041
UTEROTROPHIC ACTIVITIES IN IMMATURE FEMALE
(3-wk.old) SPRAGUE DAWLEY RATS

| | UTEROTROPHIC ACTIVITY | |
|---|---|---|
| Drug Dose (ug) | $\overline{M}$. wet wt. uterus (mg) | Ratio Drug/Estradiol |
| 1 | 11 | 0.18 |
| 4 | 13 | 0.22 |
| 16 | 17 | 0.28 |
| 64 | 16 | 0.27 |
| 128 | 14 | 0.23 |
| 256 | 15 | 0.25 |
| 512 | 19 | 0.32 |

| | ANTI-UTEROTROPHIC ACTIVITY (In the presence of 60 ug of Estradiol Benzoate) | |
|---|---|---|
| Drug Dose (ug) | $\overline{M}$ wet wt. uterus (mg) | Percent Inhibition |
| 1 | 56 | 8 |
| 4 | 53 | 14 |
| 16 | 56 | 8 |
| 64 | 58 | 4 |
| 128 | 57 | 6 |
| 256 | 53 | 14 |
| 512 | 49 | 22 |

$\overline{M}$ Control - 10 mg
$\overline{M}$ Estradiol - 60 mg

A-061
UTEROTROPHIC ACTIVITIES IN IMMATURE FEMALE
(3-wk.old) SPRAGUE DAWLEY RATS

| | UTEROTROPHIC ACTIVITY | |
|---|---|---|
| Drug Dose (ug) | $\overline{M}$. wet wt. uterus (mg) | Ratio Drug/Estradiol |
| 1 | 21.3 | 0.28 |
| 4 | 19.7 | 0.22 |
| 16 | 17.8 | 0.15 |
| 64 | 9.3 | 0 |
| 128 | 12.1 | 0 |
| 256 | 12.5 | 0 |
| 512 | 21.3 | 0.24 |

| | ANTI-UTEROTROPHIC ACTIVITY (In the presence of 60 ug of Estradiol Benzoate) | |
|---|---|---|
| Drug Dose (ug) | $\overline{M}$. wet wt. uterus (mg) | Percent Inhibition |
| 1 | 25.6 | 55.4 |
| 4 | 29.1 | 41.9 |

A-061
UTEROTROPHIC ACTIVITIES IN IMMATURE FEMALE
(3-wk.old) SPRAGUE DAWLEY RATS

| 16 | 28.4 | 44.6 |
| 64 | 28.3 | 45.0 |
| 128 | 25.0 | 57.7 |
| 256 | 23.8 | 62.3 |
| 512 | 25.8 | 54.6 |

$\overline{M}$ Control - 14 mg
$\overline{M}$ Estradiol - 40 mg

A-077
UTEROTROPHIC ACTIVITIES IN IMMATURE FEMALE
(3-wk.old) SPRAGUE DAWLEY RATS

| | UTEROTROPHIC ACTIVITY | |
| --- | --- | --- |
| Drug Dose (ug) | $\overline{M}$. wet wt. uterus (mg) | Ratio Drug/Estradiol |
| 1 | 16.0 | 0.07 |
| 4 | 13.5 | 0.0 |
| 16 | 27.3 | 0.51 |
| 64 | 33.9 | 0.76 |
| 128 | 42.2 | 1.07 |
| 256 | 36.0 | 0.84 |
| 512 | 43.2 | 1.12 |

| | ANTI-UTEROTROPHIC ACTIVITY (In the presence of 60 ug of Estradiol Benzoate) | |
| --- | --- | --- |
| Drug Dose (ug) | $\overline{M}$. wet wt. uterus (mg) | Percent Inhibition |
| 1 | 32.6 | 28.8 |
| 4 | 29.1 | 42.3 |
| 16 | 35.4 | 48.1 |
| 64 | 27.4 | 48.8 |
| 128 | 31.1 | 34.6 |
| 256 | 29.1 | 42.3 |
| 512 | 24.7 | 59.2 |

$\overline{M}$ Control - 14 mg
$\overline{M}$ Estradiol - 40 mg

ANIMAL STUDIES (A-100)
UTEROTROPHIC ACTIVITIES IN IMMATURE FEMALE
(3-wk.old) SPRAGUE DAWLEY RATS

| | UTEROTROPHIC ACTIVITY | |
| --- | --- | --- |
| Drug Dose (ug) | $\overline{M}$. wet wt. uterus (mg) | Ratio Drug/Estradiol |
| 1 | 6 | 0.10 |
| 4 | 10 | 0.16 |
| 16 | 2 | 0.03 |
| 64 | 14 | 0.23 |
| 128 | 9 | 0.15 |
| 256 | 10 | 0.16 |
| 512 | 9 | 0.15 |

| | ANTI-UTEROTROPHIC ACTIVITY | |
| --- | --- | --- |
| Drug Dose (ug) | $\overline{M}$. wet wt. uterus (mg) | Percent Inhibition |
| 1 | 43 | 37 |
| 4 | 29 | 67 |
| 16 | 28 | 69 |
| 64 | 28 | 69 |
| 128 | 27 | 71 |
| 256 | 25 | 76 |
| 512 | 28 | 69 |

$\overline{M}$ Control - 14 mg
$\overline{M}$ Estradiol - 60 mg

ANIMAL STUDIES (A-111)
UTEROTROPHIC ACTIVITIES IN IMMATURE FEMALE
(3-wk.old) SPRAGUE DAWLEY RATS

| | UTEROTROPHIC ACTIVITY | |
| --- | --- | --- |
| Drug Dose (ug) | $\overline{M}$. wet wt. uterus (mg) | Ratio Drug/Estradiol |
| 1 | 7 | 0.17 |
| 4 | 7 | 0.17 |
| 16 | 9 | 0.15 |
| 64 | 8 | 0.13 |
| 128 | 17 | 0.28 |
| 256 | 15 | 0.25 |
| 512 | 9 | 0.15 |

| | ANTI-UTEROTROPHIC ACTIVITY | |
| --- | --- | --- |
| Drug Dose (ug) | $\overline{M}$. wet wt. uterus (mg) | Percent Inhibition |
| 1 | 48 | 24 |
| 4 | 40 | 40 |
| 16 | 37 | 43 |
| 64 | 38 | 44 |
| 128 | 38 | 44 |
| 256 | 41 | 38 |
| 512 | 39 | 42 |

$\overline{M}$ Control - 10 mg
$\overline{M}$ Estradiol - 60 mg

COLONY FORMING ASSAY

Cell Culture and Growth Conditions

A soft-agar assay was used to investigate the influence of the synthesized agents on the colony formation of an estrogen dependent human breast carcinoma cell line-ZR-75-1 in culture.

Figure 10:
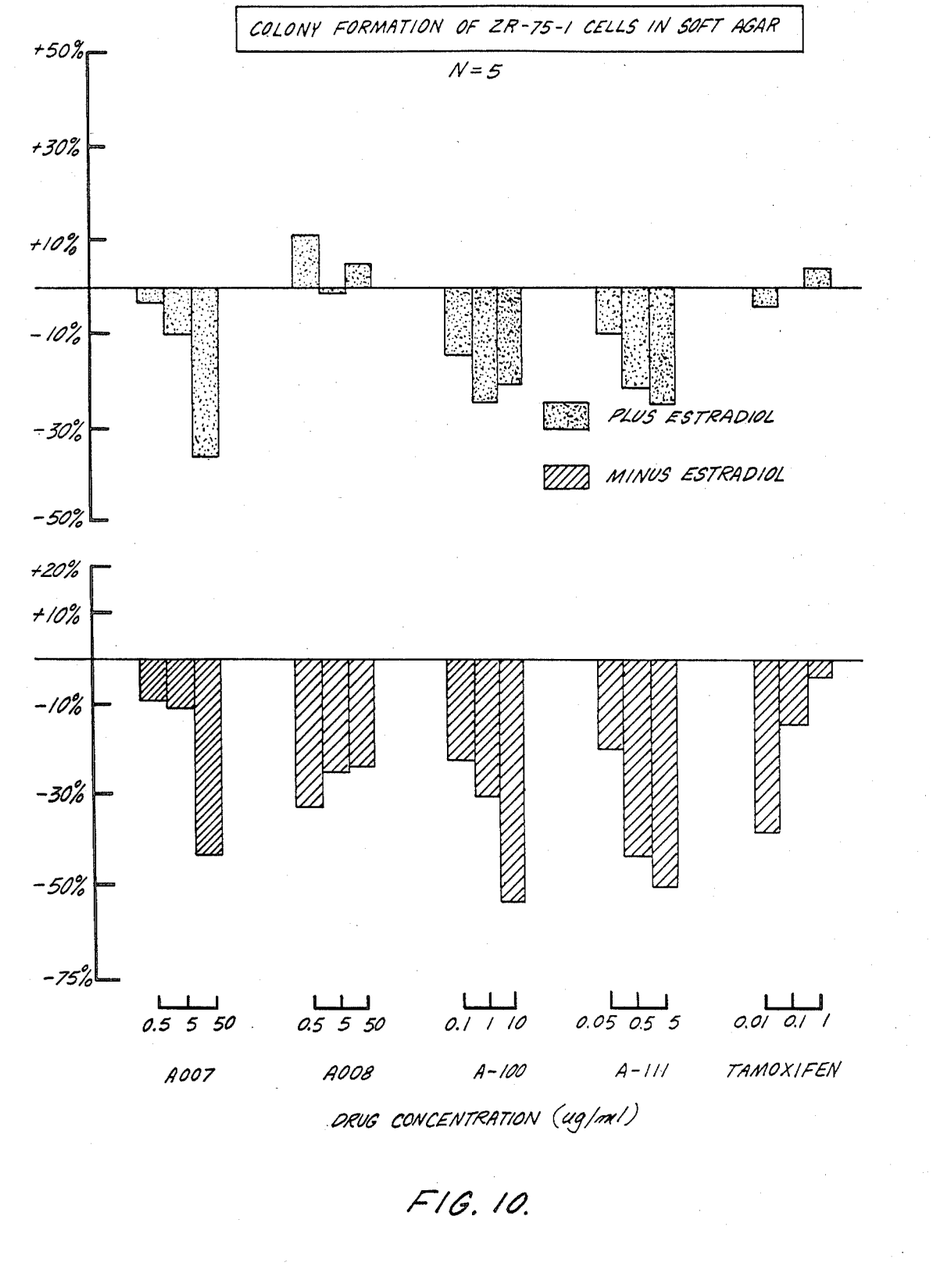
FIG. 10 is a bar graph showing colony formation of ZR-75-1 cells in soft agar for compounds A-007, A-008, A-100, A-111 and tamoxifen.

An ER and PR positive human breast carcinoma cell line ZR-75-1 was obtained from the American Type Culture Collection (Rockville, MD), which was derived from a malignant ascitic effusion (Engel et al, 1978). The cells were grown as anchoring-dependent cultures in plastic flasks (FIG. 10), nourished with RPMI-1640 medium (GIBCO, Grand Island, NY) supplemented with 10–20% fetal calf serum (GIBCO) and antibiotics (100 U/ml penicillin; 100 ug/ml streptomycin). The flasks were incubated at 37° C. in a $CO_2$ incubator, the medium changed every 2–3 days, and the cells diluted by trypsinization at approaching confluency. Under experimental conditions these cells had a population doubling time of 94 hr. The saturation density was $1.92 \times 10^8$ cells/cm$^2$. Cell counts and viability were determined with a hemacytometer and the trypan blue exclusion procedure.

Semi-confluent cultures of ZR-75-1 cells were removed from the culture flasks with a 0.05% trypsin/0.02% versene mixture (GIBCO), washed in Hanks' balanced salt solution (GIBCO), and then resuspended in an enriched CMRL medium (GIBCO) containing supplements of nutrients and antibiotics as described by Hamburger and Salmon (1977) except that the spleen macrophage colony stimulating factor was not used, and that CaCl and DEAE-dextran were reduced to 1/10 and 1/5 of the quantities, respectively. Half of the cells was exposed to 3 log concentrations (0.01, 0.1 and 1.0 ug/ml) of tamoxifen (tamoxifen citrate, Stuart Pharmaceuticals, Wilmington, DE) at 37° C. for 1 hr. Under paired conditions, the other half of the cells was preincubated with 0.1 mM 17-beta-estradiol (Sigma Chemical Co., St. Louis, MO) for 30–60 min prior to exposure to Tamoxifen.

Identical procedures were used in which the test compounds A-007 through A-111 (Table 2) were added instead of the tamoxifen citrate to evaluate their cytotoxic responses.

After incubation with the drug, melted Bacto-agar (Difco Laboratories, Inc., Detroit, MI) was added to the cell suspension to a final concentration of 0.3% agar, and the mixture plated in a 35 mm plastic tissue culture dish on a feeder layer containing an enriched McCoy's 5A medium and 0.5% agar as described by Hamburger and Salmon (1977), except for the addition of 2-mercaptoethanol (5 mM) and the reduction of DEAE-dextran to 1/5 of the quantity. The seeding density for ZR-75-1 cells in this study was kept between $1-5 \times 10^4$ cells per dish and the plates incubated at 37° C. in a $CO_2$ incubator. Incubation was continued for another 3-4 weeks and the plates were examined under an inverted phase contrast microscope. Since these cells grew as tight aggregates in soft-agar, it was not possible to determine the number of cells in each growth. An ocular micrometer was instead used to count colonies 30 um or larger in size. Plating efficiency, defined as the number of colonies formed per 100 viable cells plated, was compared between groups. The effects of tamoxifen A-007-A-111 on the development of ZR-75-1 cells in soft-agar were measured as % of inhibition or % of stimulation of their dependent controls. The results are shown graphically in the drawings.

METHOD OF TREATMENT

Three of six cases treated with 4,4' dihydroxyphenylbenzyl-4-nitrophenyl hydrazone (DPNH) are reviewed.

Case 1:

A 36 year old black female with advanced breast cancer developed a recurrence on her left chest wall at the site of her original mastectomy scar and in the field of previous irradiation. She did not have any other sites of involvement. She was treated with a 20% solution of 4,4'-Dihydroxybenzophenone-4-nitrophenylhydrazone in propylene glycol-dimetylsulfoxide (DMSO): 50/50 ratio as a topical preparation. The solution was applied four times a day to the lesion and covered by gauze bandages. Over a four week period, the lesion underwent scar formation and healed completely. The area of original involvement was totally healed with no scarring after four months. The treatment was stopped after a total period of ten weeks. She was on no additional medication after that.

Case 2:

A 78 year old white female presented with advanced breast cancer spread to the chest wall just above the site of her mastectomy scar. Again, this site had been previously irradiated and grafted. Additional surgery and irradiation could not be offered. She was treated with a 20% solution of 4,4'-Dihydroxybenzophenone-4-nitrophenylhydrazone in propylene glycol-dimethyl sulfoxide (DMSO): 50/50 ratio as a topical preparation. The solution was applied four times a day to the lesion and covered by gauge bandages. Over a two month period of daily applications, the lesion totally healed with granulation tissue formation and no cancer present.

Case 3:

A 84 year old white female with extensive skin metastasis from breast cancer was evaluated. The lesions were continuous over the right chest wall, back and abdomen. She had not responded to intravenous chemotherapy. She was treated with a 20% solution of 4,4'-Dihydroxybenzophenone-4-nitrophenylhydrazone in propylene glycol-dimethylsulfoxide (DMSO): 50/50 ratio as a topical preparation, the solution was applied twice a day to the lesions and covered by gauze bandages. Over a three month period there was a 75% dissappearance of the lesions with healing. The patient remained in therapy. The chest wall was 75% clear with good skin healing. There was still 25% cancer involvement but the response was dramatic for such a large area.

I claim:

1. A compound of the formula wherein R is hydroxy, $R^1$ is carbon, $R^2$ is hydroxyphenyl, and X is hydrogen.

2. A compound of the formula wherein R is hydrogen, hydroxy or methoxy; $R^1$ is carbon or nitrogen; $R^2$ is methyl, phenyl, hydroxyphenyl or methoxyphenyl; X is azidophenyl.

3. A compound of the formula wherein R is hydrogen, hydroxy or methoxy; $R^1$ is carbon or nitrogen; $R^2$ is methyl, phenyl, hydroxyphenyl, or methoxyphenyl; X is aminophenyl.

4. A compound of the formula wherein R is hydrogen, hydroxy or methoxy; R¹ is carbon or nitrogen; R² is methyl, phenyl or methoxyphenyl; X is azido; and Y is nitro or hydrogen.

5. A composition comprising a pharmaceutically inert carrier and the compound of claim 2 in an amount of said compound sufficient to impair growth of an estrogen dependent tumor cell.

6. A composition comprising a pharmaceutically inert carrier and the compound of claim 3 in an amount of said compound sufficient to impair growth of an estrogen dependent tumor cell.

7. A composition comprising a pharmaceutically inert carrier and the compound of claim 4 in an amount of the compound sufficient to impair growth of an estrogen dependent tumor cell.

8. A composition comprising a pharmaceutically inert carrier and, in an amount sufficient to impair growth of an estrogen dependent tumor cell, a compound of the formula wherein R is hydrogen, hydroxy or methoxy; R¹ is carbon or nitrogen; R² is methyl, phenyl, hydroxyphenyl, methoxyphenyl or dimethoxyphenyl; X is azidophenyl, aminophenyl, nitrophenyl or dinitrophenyl.

9. The composition of claim 8 wherein R is hydroxy, R¹ is carbon, R² is methyl, X is dinitrophenyl.

10. The composition of claim 8 wherein R is hydrogen, R¹ is carbon, R² is phenyl, X is dinitrophenyl.

11. The composition of claim 8 wherein R is hydroxy, R¹ is carbon, R² is phenyl, X is dinitrophenyl.

12. The composition of claim 8 wherein R is methoxy, R¹ is carbon, R² is 4-methoxyphenyl, X is dinitrophenyl.

13. The composition of claim 8 wherein R is hydrogen, R¹ is nitrogen, R² is 3,4 dimethoxyphenyl, X is dinitrophenyl.

14. The composition of claim 8 wherein R is hydrogen, R¹ is nitrogen, R² is 4-methoxyphenyl, X is dinitrophenyl.

15. The composition of claim 8 wherein R is hydroxy, R¹ is carbon, R² is 4-hydroxyphenyl, X is nitrophenyl.

16. The composition of claim 8 wherein R is hydroxy, R¹ is carbon, R² is 4-hydroxyphenyl, X is azidophenyl.

17. The composition of claim 8 wherein R² is hydroxyphenyl.

18. The composition of claim 8 wherein R² is methoxyphenyl.

19. The composition of claim 8 wherein R² is dimethoxyphenyl.

20. The composition of claim 8 wherein X is azidophenyl.

21. The composition of claim 8 wherein X is aminophenyl.

22. The composition of claim 8 wherein X is nitrophenyl.

23. The composition of claim 8 wherein X is dinitrophenyl.

24. The composition of claim 8 wherein R is hydrogen.

25. The composition of claim 8 wherein R is hydroxy.

26. The composition of claim 8 wherein R is methoxy.

27. The composition of claim 8 wherein R¹ is carbon.

28. The composition of claim 8 wherein R¹ is nitrogen.

29. The composition of claim 8 wherein R² is methyl.

30. The composition of claim 8 wherein R² is phenyl.

31. A composition comprising a pharmaceutically inert carrier and, in an amount sufficient to impair growth of an estrogen dependent tumor cell, a compound of the formula wherein R is hydrogen, hydroxy or methoxy; R¹ is carbon or nitrogen; R² is phenyl, hydroxyphenyl, methoxyphenyl or dimethoxyphenyl; and X is hydrogen.

32. The composition of claim 31 wherein R² is hydroxyphenyl.

33. The composition of claim 31 wherein R² is methoxyphenyl.

34. The composition of claim 31 wherein R² is dimethoxyphenyl.

35. A composition comprising a pharmaceutically inert carrier and, in an amount sufficient to impair growth of an estrogen dependent tumor cell, a compound of formula wherein R is hydroxy; R¹ is carbon or nitrogen; R² is methyl, phenyl, hydroxyphenyl, methoxyphenyl or dimethoxyphenyl; X is hydrogen, azidophenyl, aminophenyl, nitrophenyl or dinitrophenyl.

36. A composition comprising a pharmaceutically inert carrier and, in an amount sufficient to impair growth of an estrogen dependent tumor cell, a compound of the formula wherein R is hydrogen, hydroxy or methoxy; R¹ is nitrogen; R² is phenyl, hydroxyphenyl, methoxyphenyl or dimethoxyphenyl; and X is hydrogen, azidophenyl, aminophenyl, nitrophenyl or dinitrophenyl.

37. The composition of claim 36 wherein $R^2$ is hydroxyphenyl.

38. The composition of claim 36 wherein $R^2$ is methoxyphenyl.

39. The composition of claim 36 wherein X is azidophenyl.

40. The composition of claim 36 wherein X is aminophenyl.

41. The composition of claim 36 wherein X is nitrophenyl.

42. The composition of claim 36 wherein X is dinitrophenyl.

43. The composition of claim 36 wherein R is hydrogen.

44. The composition of claim 36 wherein R is hydroxy.

45. The composition of claim 36 wherein R is methoxy.

46. The composition of claim 36 wherein $R^2$ is phenyl.

47. A method of treating a recurrence of breast cancer on the skin surface, comprising the step of applying a therapeutically effective amount of a compound of the formula to the affected surface of the skin, wherein R is hydrogen, hydroxy or methoxy; $R^1$ is carbon or nitrogen; $R^2$ is methyl, phenyl, hydroxyphenyl, methoxyphenyl or dimethoxyphenyl; X is hydrogen, azidophenyl, aminophenyl, nitrophenyl or dinitrophenyl.

48. The method of claim 47 wherein a pharmaceutically inert carrier is added to the compound before application to the skin surface.

49. The method of claim 48 wherein the inert carrier is comprised of dimethylsulfoxide.

50. The method of claim 47 wherein X is azidophenyl, aminophenyl, or nitrophenyl.

51. The method of claim 50 wherein X is azidophenyl.

52. The method of claim 47 wherein X is aminophenyl.

53. The method of claim 47 wherein X is nitrophenyl.

54. The method of claim 47 wherein X is dinitrophenyl.

55. The method of claim 47 wherein $R^2$ is phenyl.

56. The method of claim 47 wherein $R^2$ is hydroxyphenyl.

57. The method of claim 47 wherein $R^2$ is methoxyphenyl.

58. The method of claim 47 wherein R is hydrogen.

59. The method of claim 47 wherein R is hydoxy.

60. The method of claim 47 wherein R is methoxy.

61. The method of claim 47 wherein $R^1$ is carbon.

62. The method of claim 47 wherein $R^1$ is nitrogen.

63. The method of claim 47 wherein $R^2$ is methyl.

64. The method of claim 47 wherein $R^2$ is dimethoxyphenyl.

65. The method of claim 47 wherein X is hydrogen.

66. A composition comprising a pharmaceutically inert carrier and, in an amount sufficient to impair growth of an estrogen dependent tumor cell, a compound of the formula wherein R is hydroxy; $R^1$ is carbon or nitrogen; $R^2$ is methoxyphenyl or dimethoxyphenyl; X is nitro, amino or azido; and Y is nitro or hydrogen.

67. A composition comprising a pharmaceutically inert carrier and, in an amount sufficient to impair growth of an estrogen dependent tumor cell, a compound of the formula wherein R is hydrogen, hydroxy or methoxy; $R^1$ is carbon or nitrogen; $R^2$ is phenyl, hydroxyphenyl, methoxyphenyl or dimethoxyphenyl; X is hydrogen, azidophenyl, aminophenyl, nitrophenyl or dinitrophenyl.

68. The composition of claim 67 wherein $R^2$ is hydroxyphenyl.

69. The composition of claim 67 wherein $R^2$ is methoxyphenyl.

70. The composition of claim 67 wherein $R^2$ is dimethoxyphenyl.

71. A composition comprising a pharmaceutically inert carrier and, in an amount sufficient to impair growth of an estrogen dependent tumor cell, a compound of the formula wherein R is hydrogen, hydroxy, or methoxy; $R^1$ is nitrogen; $R^2$ is methyl, phenyl, hydroxyphenyl, methoxyphenyl or dimethoxyphenyl; X is azidophenyl, aminophenyl, nitrophenyl or dinitrophenyl.

72. The composition of claim 71 wherein X is azidophenyl.

73. The composition of claim 71 wherein X is aminophenyl.

74. The composition of claim 71 wherein X is nitrophenyl.

75. The composition of claim 71 wherein X is dinitrophenyl.

76. A composition comprising a pharmaceutically inert carrier and, in an amount sufficient to impair growth of an estrogen dependent tumor cell, a compound of the formula wherein R is hydrogen, hydroxy or methoxy; $R^1$ is carbon; $R^2$ is methyl, phenyl, hydroxyphenyl, methoxyphenyl or dimethoxyphenyl; X is hydrogen, aminophenyl, nitrophenyl, dinitrophenyl, or azidophenyl.

77. The composition of claim 76 wherein X is nitrophenyl or azidophenyl.

78. The composition of claim 76 wherein $R^2$ is phenyl.

79. A method of impairing growth of estrogen dependent tumor cells in a host organism, comprising the step of administering a therapeutically effective amount of a compound of the formula to the host organism, wherein R is hydrogen, hydroxy or methoxy; $R^1$ is carbon or nitrogen; $R^2$ is methyl, phenyl, hydroxyphenyl, methoxyphenyl or dimethoxyphenyl; X is hydrogen, azidophenyl, aminophenyl, nitrophenyl or dinitrophenyl.

80. The method of claim 79 wherein X is azidophenyl or aminophenyl.

81. The method of claim 79 wheren X is nitrophenyl.

82. The method of claim 80 wherein $R^2$ is methoxyphenyl.

83. The method of claim 79 wherein $R^2$ is phenyl.

84. The method of claim 79 wherein $R^2$ is hydroxyphenyl.

85. The method of claim 79 wherein $R^2$ is dimethoxyphenyl.

86. The method of claim 79 wherein the compound is administered in a pharmaceutically inert carrier.

87. The method of claim 79 wherein R is hydrogen.

88. The method of claim 79 wheren R is hydroxy.

89. The method of claim 79 wherein R is methoxy.

90. The method of claim 79 wherein $R^1$ is carbon.

91. The method of claim 79 wheren $R^1$ is nitrogen.

92. The method of claim 79 wherein $R^2$ is methyl.

93. The method of claim 79 wherein X is azidophenyl.

* * * * *